United States Patent [19]

Iino et al.

[11] Patent Number: 4,784,743
[45] Date of Patent: Nov. 15, 1988

[54] OXYGEN SENSOR

[75] Inventors: Atsushi Iino, Nagoya; Nobuhide Kato, Ama, both of Japan

[73] Assignee: NGK Insulators, Ltd., Nagoya, Japan

[21] Appl. No.: 800,684

[22] Filed: Nov. 22, 1985

[30] Foreign Application Priority Data

Dec. 6, 1984 [JP] Japan .................................. 59-258080
Dec. 6, 1984 [JP] Japan .................................. 60-115576
May 29, 1985 [JP] Japan .................................. 60-115574

[51] Int. Cl.$^4$ ............................................. G01N 27/46
[52] U.S. Cl. .................................... 204/425; 204/426; 204/427
[58] Field of Search ........................... 204/15, 421–429

[56] References Cited

U.S. PATENT DOCUMENTS

| | | | |
|---|---|---|---|
| Re. 28,792 | 4/1976 | Ruka et al. | 204/425 |
| 4,359,030 | 11/1982 | Sone et al. | 204/425 |
| 4,365,604 | 12/1982 | Sone | 204/425 |
| 4,384,935 | 5/1983 | De Jong | 204/425 |
| 4,430,191 | 2/1984 | Sone et al. | 204/425 |
| 4,464,244 | 8/1984 | Uchida et al. | 204/425 |
| 4,502,939 | 3/1985 | Holfelder et al. | 204/425 |
| 4,505,807 | 3/1985 | Yamada | 204/427 |
| 4,559,126 | 12/1985 | Mase et al. | 204/426 |

FOREIGN PATENT DOCUMENTS 0100853 6/1984 Japan .................................. 204/426

Primary Examiner—T. Tung
Attorney, Agent, or Firm—Parkhurst, Oliff & Berridge

[57] ABSTRACT

An oxygen sensor element includes at least a standard electrode (i.e., reference electrode) and a measurement electrode and is made of an oxygen ion-conducting solid electrolyte and is accommodated in a casing. An airtight space formed in the oxygen sensor element or in the casing communicates with the standard electrode and is maintained substantially in an airtight state with respect to the external atmosphere. At least one pair of oxygen pump electrodes for supplying oxygen to the airtight space is arranged in the oxygen sensor element. Therefore, since it is not necessary to arrange a hole for the supply of a reference substance (such as air) in the oxygen sensor, it is possible to completely eliminate the deterioration and the damage of the oxygen sensor element due to the intrusion of water, sea water and the like from the external atmosphere.

13 Claims, 8 Drawing Sheets

FIG_2

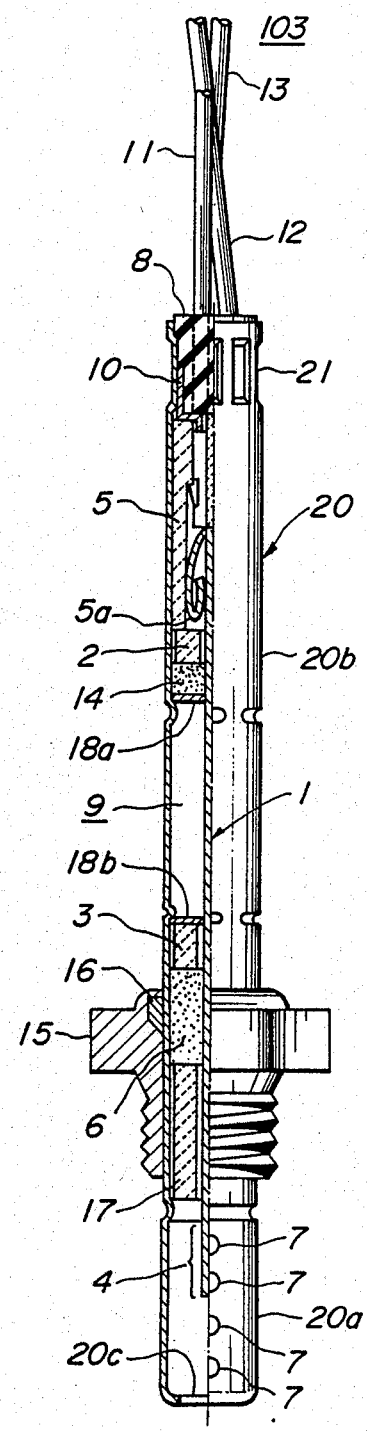
FIG_4
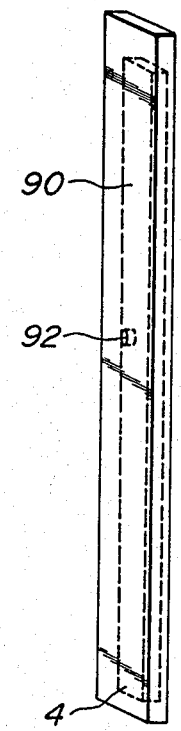
FIG_5

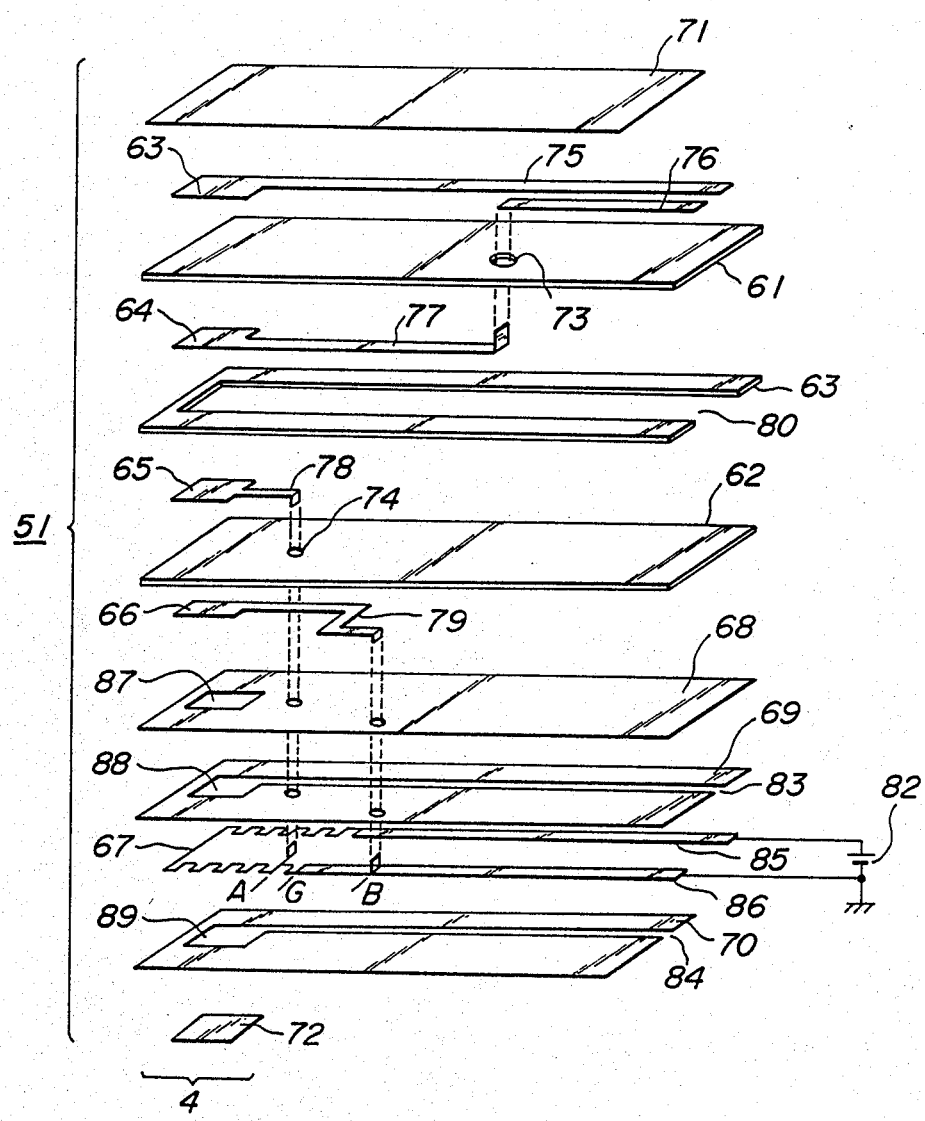
FIG_6

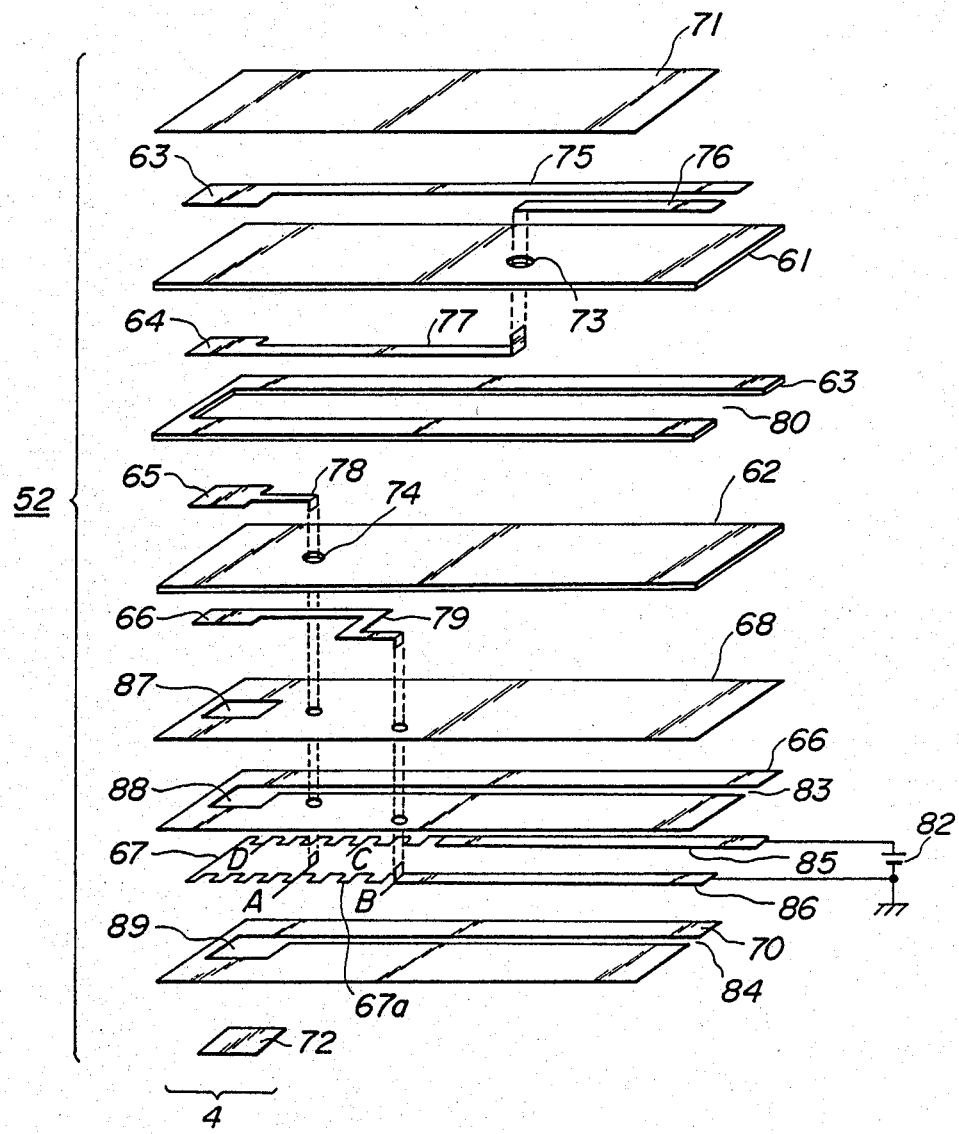
FIG_7

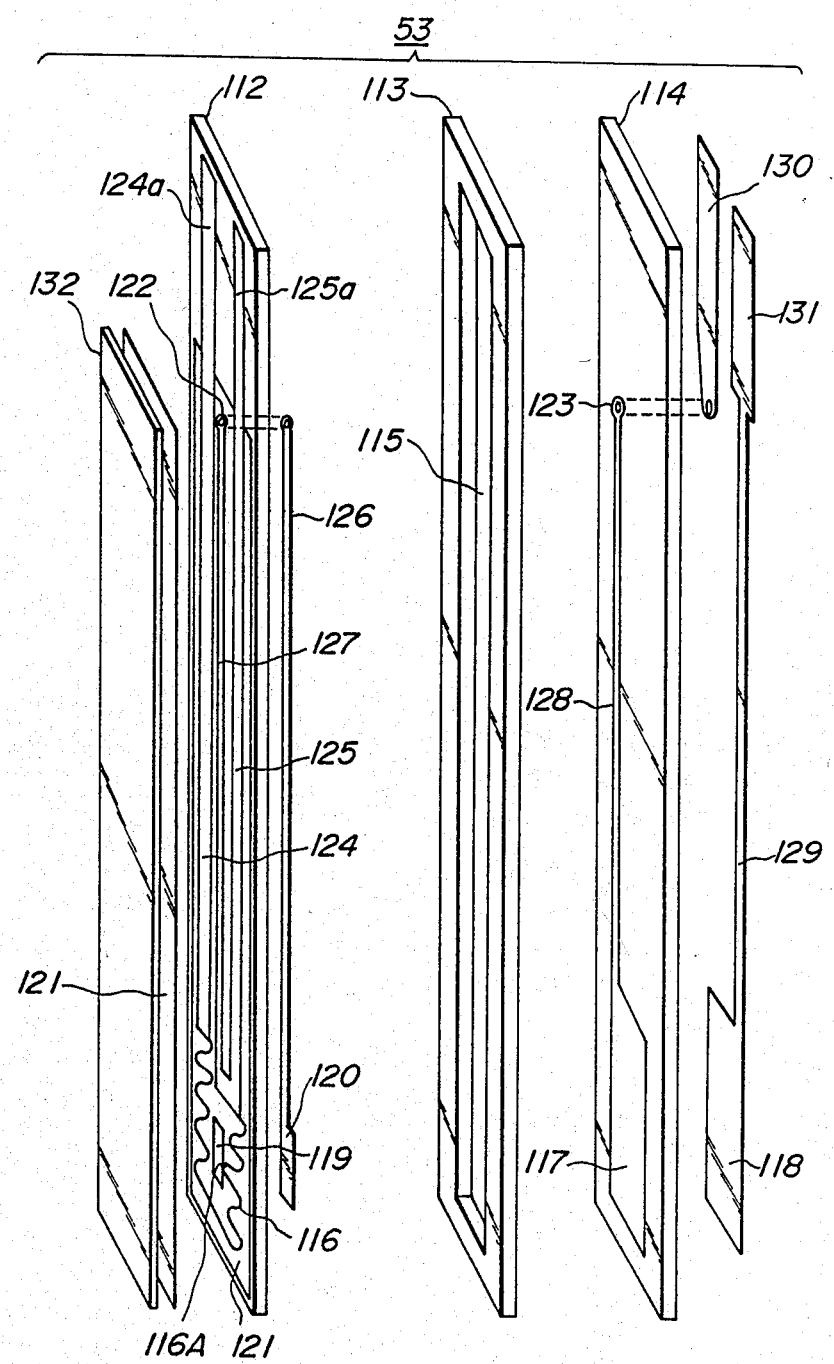

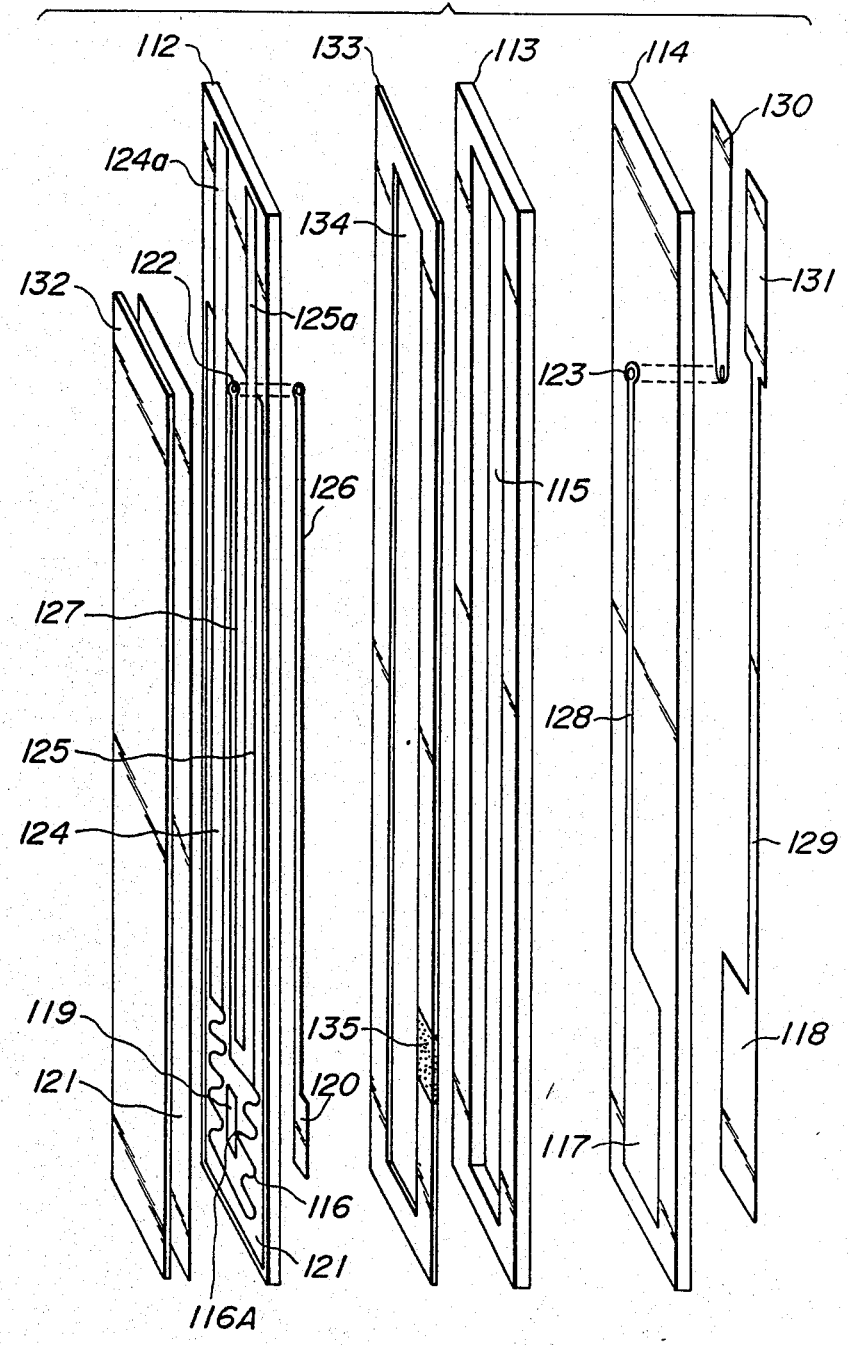

OXYGEN SENSOR

BACKGROUND OF THE INVENTION

1. Field of the Invention

The present invention relates to an oxygen sensor for detecting an oxygen concentration in a gas to be measured, especially an exhaust gas from an internal combustion engine.

2. Related Art Statement

Heretofore, there has been known an oxygen sensor used for detecting an oxygen concentration in an exhaust gas from an internal combustion engine and to provide for optimum control of a burning condition in the internal combustion engine in response to a detection signal thereof so as to eliminate undesirable components in the exhaust gas and result in fuel savings.

In general, such as oxygen sensor comprises an oxygen sensor element composed of a measurement electrode exposed to a gas to be measured such as an exhaust gas or the like, a standard electrode exposed to a standard substance having a constant oxygen concentration and an oxygen ion-conducting solid electrolyte body interposed between the measurement electrode and the standard electrode, said oxygen sensor generates a signal based on the oxygen ion conduction between both the electrodes as a detection signal. Usually, air is used as the above standard material. Therefore, the conventional oxygen sensor is provided at its outer casing surface with an air inlet for contacting the air with the standard electrode of the oxygen sensor element.

However, in the oxygen sensor provided with the air inlet, when it is mounted on the vehicle as described above, water or sea water might intrude into the oxygen sensor through the air inlet, which brings about a possibility that the oxygen sensor element might be damaged or might not be conductive. Moreover, since the oxygen sensor is used under high temperature conditions, water which intrudes into the oxygen sensor is changed into vapor to discharge the standard material such as air from the oxygen sensor, so that the detection of the oxygen concentration can not be performed effectively.

In order to solve the above problem, there has been proposed an oxygen sensor, wherein the air inlet is excluded and a small space is made in a porous body around the standard electrode, into which air, for example, oxygen from the exhaust gas, is supplied by means of an oxygen pump. In this oxygen sensor, since an excess gas in the small space is discharged through a slight gap formed therein to make an oxygen partial pressure in the small space constant, or since it is necessary to supply oxygen in the small space, an amount of which is equal to that consumed in reading an output signal of the oxygen sensor by means of an external instrument or the like, it is necessary to continuously operate the oxygen pump. In this case, since the oxygen pump does not operate effectively under low temperature, it is necessary to apply a high voltage to the oxygen pump electrode so as to operate it effectively under low temperature. However, if such high voltage is applied, electrolysis is liable to occur in the solid electrolyte, resulting in the deterioration of the oxygen sensor element. In order to avoid such a phenomenon, it is considered that the oxygen pump portion is always heated by means of a heater at a high temperature for operating the oxygen pump effectively. In this case, however, there are drawbacks that the amount of power consumption for the heater becomes large, the oxygen sensor element deteriorates rapidly due to heat from the heater and the service life of the heater becomes short.

SUMMARY OF THE INVENTION

It is, therefore, an object of the present invention to eliminate the above mentioned drawbacks and to provide an oxygen sensor which can effectively eliminate the deterioration and damage due to the intrusion of foreign matter such as water or the like from an exterior portion of the sensor.

According to the invention, there is the provision of an oxygen sensor comprising an oxygen sensor element composed mainly of an oxygen ion-conducting solid electrolyte body and provided with at least a standard electrode and a measurement electrode and a casing housing having said oxygen sensor element therein, which comprises:

- an airtight space maintained substantially in an airtight state with respect to the external atmosphere and facing said standard electrode; and
- at least one pair of oxygen pump electrodes for supplying oxygen to said airtight space through oxygen ion conduction.

Another object of the invention is to provide an oxygen sensor element preferably used as an oxygen sensor.

According to the invention, there is the provision of an oxygen sensor element comprising an oxygen ion-conducting solid electrolyte body and at least a standard electrode and a measurement electrode, which comprises;

- a gap formed in said solid electrolyte body for introducing a standard substance, said gap facing said standard electrode;
- at least one pair of oxygen pump electrodes for supplying oxygen to said gap by oxygen ion conduction;
- a heater for heating at least one of said standard electrode, measurement electrode and oxygen pump electrodes; and
- a means for dividing a voltage applied to said heater and for applying said divided voltage to said pair of oxygen pump electrodes.

Still another object of the invention is to provide an oxygen sensor element which can be used in the oxygen sensor.

According to the invention, there is also the provision of an oxygen sensor element comprising an oxygen ion-conducting solid electrolyte body and at least a standard electrode and a measurement electrode, which comprises;

- an airtight space arranged in said solid electrolyte body and maintained substantially in an airtight state with respect to the external atmosphere, and
- at least one pair of oxygen pump electrodes for supplying oxygen to said airtight space by oxygen ion conduction.

BRIEF DESCRIPTION OF THE DRAWINGS

FIG. 4 is a side elevational view of a third embodiment of the oxygen sensor according to the invention;

FIG. 5 is a perspective view of an embodiment of the oxygen sensor element preferably used in the oxygen sensor of in FIG. 4;

FIG. 6 is an exploded perspective view of a second embodiment of the oxygen element according to the invention;

FIG. 7 is an exploded perspective view of a third embodiment of the oxygen sensor element according to the invention;

FIG. 8 is an exploded perspective view of a fourth embodiment of the oxygen sensor element according to the invention; and FIG. 9 is an exploded perspective view of a fifth embodiment of the oxygen sensor element according to the invention.

DESCRIPTION OF THE PREFERRED EMBODIMENTS

Figure 1:
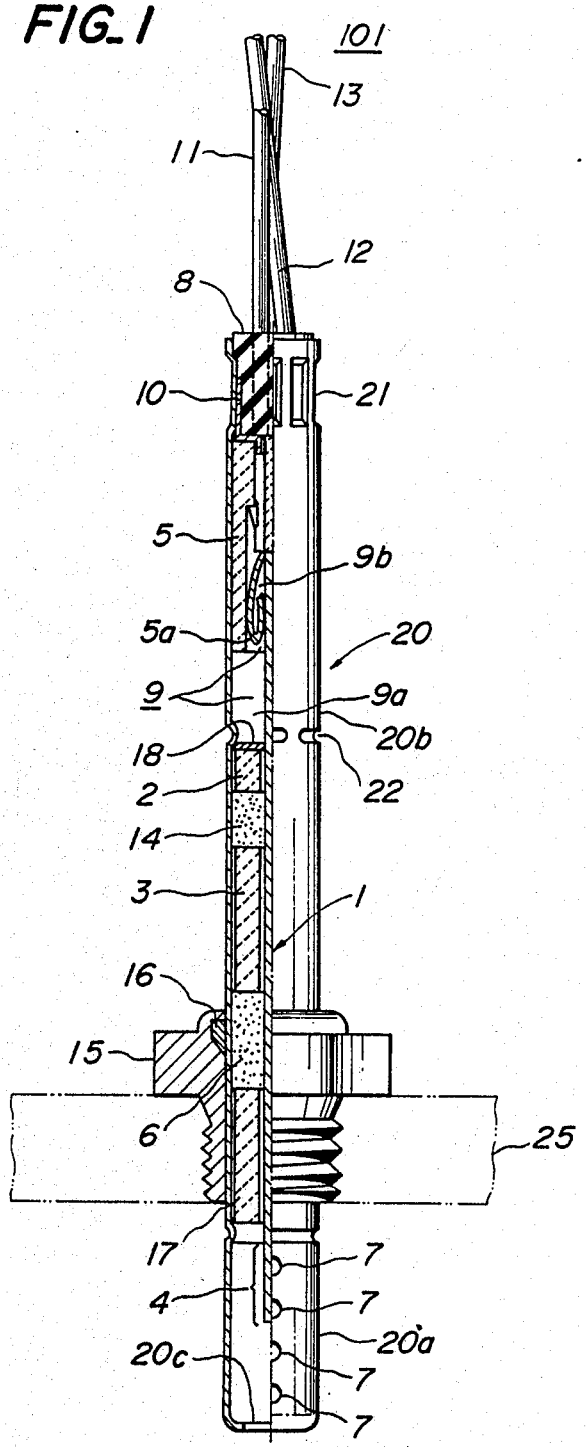
FIG. 1 is a side elevational view partly shown in section of a first embodiment of the oxygen sensor according to the invention.
Figure 2:
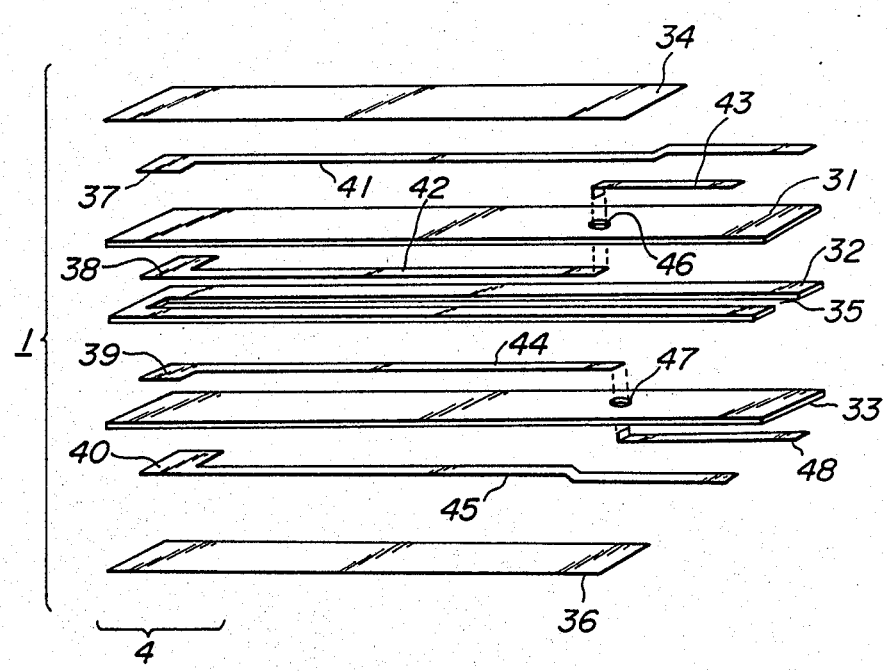
FIG. 2 is an exploded perspective view of a first embodiment of the oxygen sensor element according to the invention.

In FIG. 1 is shown a first embodiment of the oxygen sensor according to the invention, and FIG. 2 shows a first embodiment of the oxygen sensor element preferably used in the oxygen sensor of FIG. 1. In this embodiment, the oxygen sensor 101 comprises an oxygen sensor element 1 formed in a plate-like shape (i.e., an elongated planar shape) and a cylindrical protection tube 20 made of a metal as a casing housing the oxygen sensor element 1 therein.

As explodedly illustrated in FIG. 2, the oxygen sensor element 1 has such a structure that three oxygen ion-conducting solid electrolyte bodies 31–33 (hereinafter referred to as a solid electrolyte body) are piled one upon the other in a laminar arrangement, wherein the middle solid electrolyte body 32 is provided with a gap 35 extending in the longitudinal direction thereof. It should be noted that the solid electrolyte body 32 may be made of an insulative ceramic material. A measurement electrode 37 is adhered to one end portion of the upper surface of the upper solid electrolyte body 31, and a standard electrode 38 is adhered to the lower surface thereof at a position opposite to that of the measurement electrode 37 so as to face the gap 35. Moreover, a pump electrode 39 is adhered to one end portion of the upper surface of the lower solid electrolyte body 33, and the other pump electrode 40 is adhered to the lower surface thereof at a position opposite to that of the pump electrode 39.

Each of these solid electrolyte bodies 31 to 33 is made from an oxygen ion-conducting solid electrolyte consisting mainly of zirconia ($ZrO_2$) into which at least one of $Y_2O_3$, CaO, $Yb_2O_3$ and MgO is added as a stabilizer.

Further, a conductive lead member 41 connecting with the measurement electrode 37 and a part of a conductive lead member 43 connecting with the standard electrode 38 are arranged on the upper surface of the upper solid electrolyte body 31, and are covered with a protection layer 34 made of a ceramic thin film, except for right end portions of the conductive lead members 41 and 43, as illustrated in FIG. 2. Moreover, a conductive lead member 42 connecting to the standard electrode 38 is arranged on the lower surface of the upper solid electrolyte body 31, a tip of which is connected to the conductive lead member 43 by a through-hole 46.

Similarly, a conductive lead member 45 connecting to the pump electrode 40 and a part of a conductive lead member 48 connected to the pump electrode 39 are arranged on the lower surface of the lower solid electrolyte body 33, and are covered with a protection layer 36 made of a ceramic thin film except for right end portions of the conductive lead members 45, 48. Further, a conductive lead member 44 connecting to the pump electrode 39 is arranged on the upper surface of the lower solid electrolyte body 33, a tip of which is connected to the conductive lead member 48 through a through-hole 47.

As shown in FIG. 1, the protection tube 20 comprises a protection cover potion 20a surrounding an oxygen detecting portion 4 (which includes the respective electrodes 37 to 40 as shown in FIG. 2) of the oxygen sensor element 1, and a protection cylinder portion 20b housing the remaining portion of the oxygen sensor element 1 other than the oxygen detecting portion 4. In the protection cover portion 20a, four inlet holes 7 for a gas to be measured are formed at a position corresponding to each widthwise side of the oxygen sensor element 1 in the longitudinal direction as shown in FIG. 1, whereby the gas to be measured is introduced through these gas inlet holes 7 to contact with the oxygen detecting portion 4. Moreover, an opening 20c for the insertion of a jig which serves to position the oxygen sensor element 1 in the protection tube 20 is formed in the tip of the protection cover portion 20a.

Further, around the lower portion of the protection cylinder portion 20b is fixed a housing 15 which serves to secure the oxygen sensor 101 to a partition 25 for isolating the gas to be measured from the other portions, for example, a wall of an exhaust tube of a vehicle. Further, an airtight ring 16 made of stainless steel is arranged between the housing 15 and the protection cylinder portion 20b so as not to leak the gas to be measured from the boundary between the housing 15 and the protection cylinder portion 20b.

In the protection cylinder portion 20b, the middle portion of the oxygen sensor element 1 is secured by first, second and third porcelain insulators 17, 3 and 2, respectively, and first and second airtight members 6 and 14. The airtight members 6 and 14 act to not only secure the oxygen sensor element 1 but also to prevent the intrusion of the gas to be measured from the side of the protection cover portion 20a into the protection cylinder portion 20b, each of which is made from an inorganic filler such as cement, talc or the like. The first to third porcelain insulators 17, 3, 2 and the first and second airtight members 6 and 14 are positioned so as not to shift upward by a position maintaining plate 18 arranged on the upper surface of the third porcelain insulator 2 and a caulking portion 22 formed on the protection cylinder portion 20b.

In the upper part of the protection cylinder portion 20b is arranged a porcelain connector 5 for connecting lead wires 11 to 13 from external circuits and a ground wire 10 connected with the inner surface of the protection tube 20 to terminals of respective conductive lead members 41, 43, 45 and 48 for the electrodes arranged on both surfaces of the oxygen sensor element 1. Moreover, into the upper end of the protection cylinder portion 20b is placed a rubber stopper 8, through which the lead wires 11 to 13 are passed, so as to completely seal the protection cylinder portion 20b. The rubber stopper 8 is airtightly fixed by a caulking portion 21 formed on the outer periphery of the protection tube 20 at a position corresponding to the stopper.

In the porcelain connector 5 are arranged connection springs 5a, 5b, 5c, 5d (one of them is shown in FIG. 1) which are respectively brought into contact with terminals of the conductive lead members 41, 43, 45 and 48 (i.e. connection terminals) for the electrodes arranged on the oxygen sensor element 1. Among them, the connection spring 5a is connected to one of the ground wire 10 and the lead wires 11 to 13.

Between the porcelain connector 5 and the position maintaining plate 18 is formed an airtight space 9 comprising a first space 9a surrounded by the upper surface of the position maintaining plate 18, the protection cylinder portion 20b and the lower surface of the porcelain connector 5 and the second space 9b communicating with the first space, housing the porcelain connector 5 and being pluged by the lower surface of the rubber stopper 8, the lead wires 11 to 13 and the ground wire 10. The airtight space 9 is only communicated with the gap 35 facing the standard electrode 38 and the pump electrode 39 through a gap between the upper portion of the oxygen sensor element 1 and the porcelain connector 5.

In the oxygen sensor 101 of the above mentioned structure, a relatively large amount of air as a standard substance can be held in the airtight space 9 communicating with the gap 35 facing the standard electrode 38, and the airtight space 9 is airtightly isolated from the external atmosphere, so that it is possible to completely avoid the damage of the oxygen sensor due to the intrusion of foreign matter such as water, sea water and the like, as in the past.

Moreover, as to oxygen consumption in the airtight space 9 accompanied with the operation of the oxygen sensor, oxygen is supplied into the gap 35 from the gas to be measured by operating the oxygen pump electrodes 39, 40 (the portion of the oxygen sensor element including the oxygen pump electrodes forms an oxygen detecting portion 4 exposed to the gas to be measured) and then reserved in the airtight space 9. In this case, since the volume of the airtight space 9 is large, it is sufficient to perform the supply of oxygen into the airtight space 9 only under a relatively high temperature in the operation of the oxygen sensor, and it is possible to operate the oxygen pump effectively even if a voltage applied to the oxygen pump electrodes 39, 40 is low. Therefore, when the temperature of the position of the oxygen pump electrodes 39, 40 becomes lower, since the voltage applied to these electrodes is low, electrolysis of the oxygen ion-conducting solid electrolyte body and the associated degradation of the oxygen sensor element does not occur. At the lower temperature, the operation of the oxygen pump electrodes 39, 40 somewhat lowers, but the volume of the airtight space 9 is large, so that it is not always required to operate the oxygen pump in the operation of the oxygen sensor.

Figure 3:
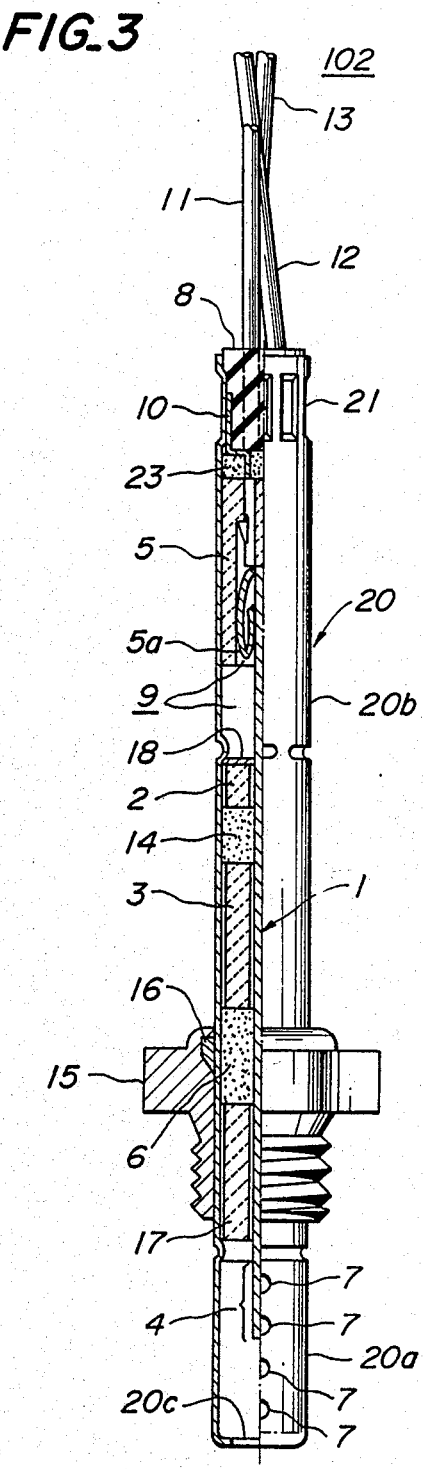
FIG. 3 is a side elevational view partly shown in section of a second embodiment of the oxygen sensor according to the invention.

FIG. 3 shows a second embodiment of the oxygen sensor according to the invention. In this embodiment, the oxygen sensor 102 has the same structure as that of the first embodiment illustrated in FIG. 1, except that a partition 23 is arranged between the rubber stopper 8 and the porcelain connector 5 to airtightly isolate them to each other (an oxygen sensor element 51 as mentioned later may be used instead of the oxygen sensor element 1). If the rubber stopper 8 is heated to a higher temperature region, an organic gas inherent to the rubber material may be generated, which then fills the airtight space 9. The partition 23 acts to prevent the contamination of the airtight space 9 with such an organic gas. Therefore, it is considered that when the rubber sopper 8 is formed by another material, the use of the partition 23 is useless.

FIG. 4 shows a third embodiment of the oxygen sensor according to the invention. In the oxygen sensor 103 of this embodiment, only the position of the airtight space 9 is different from that of the first embodiment shown in FIG. 1. That is, the airtight space 9 for holding the standard gas is airtightly maintained with respect to the gas to be measured by the first airtight member 6 made of an inorganic filler such as talc, cement or the like on one hand, and with respect to gas components, which may be produced from the organic material such as the rubber stopper or the like at higher temperature, by the second airtight member 14 made of a fused glass or an inorganic filler such as talc, cement or the like on the other hand. Therefore, the oxygen sensor element 1 comprises an inlet hole 92 communicating with the airtight space 9 at a position corresponding to the airtight space 9 as shown in FIG. 5, wherein an upper end portion of a gap 90 (corresponding to the gap 35 of FIG. 1) is airtightly closed. For example, such an oxygen sensor element may be formed in such a manner that the right end portion of the gap 35, as shown in FIG. 2, is airtightly closed and a through-hole communicating with the airtight space through the solid electrolyte body 31 and the protection layer 37 is formed as the inlet hole.

Particularly, it is preferable to use the oxygen sensor of the second and third embodiments when the rubber stopper 8 is exposed to a relatively high temperature region, for example, when the oxygen sensor is mounted to an engine or near the engine producing a high exhaust gas temperature.

In the embodiments mentioned above, the oxygen pump (oxygen pump electrodes 39, 40) is arranged at the oxygen detecting portion 4, but it is possible to arrange the oxygen pump at another portions. For instance, the oxygen pump may be arranged so that oxygen is supplied into the airtight space 9 from the atmosphere instead of the gas to be measured. Moreover, the shapes, numbers and materials of the protection tube 20, the porcelain insulators 17, 2, 3 and the airtight members 6, 14 are not limited to the embodiments mentioned above. Therefore, it is a matter of course that the position of the airtight space 9 may be located at any portion of the oxygen sensor if the airtight space 9 is maintained in the airtight state and communicated with the gap 35 facing the standard electrode 38.

In FIG. 6 is shown a second embodiment of the oxygen sensor element according to the invention. In this embodiment, the oxygen sensor element 51 is assembled in the same manner as in the first embodiment of FIG. 2.

As shown in FIG. 6, a measurement electrode 63 and a standard electrode 64 are respectively formed on upper and lower surfaces of a solid electrolyte body 61, and a conductive lead member 75 for the measurement electrode 63 is also formed on the upper surface of the solid electrolyte body 61. Conductive leads members 77 and 76 for the standard electrode 64 are respectively formed on the lower and upper surfaces of the solid electrolyte body 61, and are electrically connected with each other via a through-hole 73. The upper surface of the solid electrolyte body 61 including the measurement electrode 63 and the conductive lead members 75, 76 is covered with a protection layer 71 so as to expose the right side end portion thereof to the external atmosphere. On the lower surface of the solid electrolyte body 61 is arranged an insulation plate 63 made of porcelain ceramic having a gap 80, and also on the lower surface of the insulation plate 63 is arranged another solid electrolyte body 62. Moreover, pump electrodes 65 and 66 are respectively arranged on the upper and lower surfaces of the solid electrolyte body 62 at the left side end portion thereof as shown in FIG. 6.

Furthermore, a resistance heating element 67 and two lead members 85, 86, which are sandwiched between heater protection layers 69 and 70, are arranged on the lower surface of the solid electrolyte body 62 through an insulation layer 68. Further, windows 87, 88 and 89 each facing the pump electrode 66 are respectively formed in the insulation layer 68 and the heater protection layers 69, 70, and further the pump electrode 66 is substantially covered with a porous protection layer 72. Moreover, slits 83 and 84 are respectively arranged in the heater protection layers 69 and 70 so as to ensure the insulation between the lead members 85 and 86.

In the illustrated embodiment, a conductive lead member 78 of the pump electrode 65 is connected to a point A in the heating element 67 via a through-hole 74, and a conductive lead member 79 of the pump electrode 66 is connected to a point B of the conductive lead member 86. Therefore, across the pump electrodes 65 and 66 is applied a voltage obtained by dividing a voltage from a heater power source 82 through the heating element 67.

The oxygen sensor using the oxygen sensor element of the above mentioned structure has the same effects as those of the first embodiment because the gap 80 is communicated with the airtight space 9 of FIG. 1. That is, the standard substance can be held in the airtight space and the occurrence of trouble due to the intrusion of the foreign matter can effectively be prevented.

Further, the oxygen pump consisting of the pump electrodes 65, 66 and the solid electrolyte body 62 utilizes the power source 82 for the heating element 67, so that it is not necessary to arrange another power source for the oxygen pump. Moreover, since the number of lead members in the connecting portion (which is connected to a porcelain connector) is 4, the same porcelain connector 5, as in the first embodiment, can be utilized. Therefore, it is a matter of course that the porcelain connector 5 utilized in this second embodiment can be interchangeable with that of an oxygen sensor with a four terminal construction having no heater or oxygen pump (e.g. a connector for connecting lead members 11–13 to a circuit mounted on the vehicle).

Further, since the divided voltage of the power source 82 is applied across the pump electrodes 65 and 66, the divided voltage under low temperature becomes lower than that under high temperature if the heating element 67 is made of a material having a positive resistivity-temperature coefficient (because a rate of resistivity of the heating element 67 to total resistivity of the lead members 85, 86 is decreased at low temperature).

When the oxygen sensor is operated at a low temperature region (not more than 500° C.), it is necessary to limit the voltage applied to the oxygen pump to 2-3 V, preferably not more than 1 V, otherwise the oxygen sensor element deteriorates. In this connection, according to the invention, a part of the voltage from the power source is divided by the heating element 67 having a positive resistivity-temperature coefficient and applied across the pump electrodes 65, 66, whereby a voltage of about 2 V (in this case, a voltage of the heater power source is about 12 to 16 V) can be applied across the pump electrodes at high temperature to supplement oxygen into the airtight space 9 and the divided voltage can be reduced to about 1 V at low temperature to prevent the deterioration of the oxygen sensor element. This is very advantageous in case that the oxygen sensor is mounted onto a vehicle and often brought into contact with an exhaust gas having a relatively low temperature in the starting of engine.

Although the efficiency of the oxygen pump lessens at low temperature, since the volume of the airtight space 9 is large, it is possible to operate the oxygen sensor effectively. Therefore, the airtight space 9 is sufficient to have a volume for holding the standard substance (oxygen content is above a few percent), and consequently it is most preferable to utilize an empty space formed in the protection tube 20. Further, since a certain amount of the standard substance can be held in the airtight space, it is not always necessary to operate the oxygen pump, so that it is needless to increase a heater input for heating the oxygen pump. Therefore, the power consumption can be reduced, and the deterioration of the oxygen sensor element due to the heat can be removed.

In the embodiment of FIG. 6, if use is made of the conductive lead member 86 having a fairly large resistivity, the heating element 67 is made of a material having a positive resistivity-temperature coefficient and the point A is set near the conductive lead member 86 as far as possible, the divided voltage at low temperature can be made larger that that at high temperature. Thus, a relatively high divided voltage (which is preferably not more than an electrically decomposed voltage of the oxygen ion-conducting solid electrolyte body) can be applied to the oxygen pump at low temperature so as to make a transportation amount of oxygen larger, while a relatively low divided voltage (the oxygen transportation amount becomes larger even at the low voltage because the value of resistivity of the solid electrolyte body becomes small) can be applied at high temperature so as to prevent the excess oxygen transportation.

Here, it is assumed that a connection between the conductive lead member 86 and the heating element 67 is a point G, and a total resistivity of the conductive lead members 85, 86 is $R_L$, a total resistivity of the heating element 67 is $R_H$, a resistivity between points B and G on the conductive lead member 86 is $R_B$, and a resistivity between points A and G on the heating element 67 is $R_A$. In this case, the point A or the point B is set to satisfy the following equation.

$$R_A = (R_H/R_L) \times R_B$$

When the voltage of the power source is $V_0$, the divided voltage V applied across the oxygen pump electrodes is obtained from the following equation:

$$V = \frac{R_A + R_B}{R_H + R_L} \times V_0 = \frac{R_B}{R_L} \times V_0$$

Therefore, substantially constant voltage can be supplied across the pump electrodes irrespective of the presence of the heating element (the fluctuation of $V_0$ and temperature distribution of the heating element results in the some fluctuation of the divided voltage.) According to the embodiment mentioned above, it is possible to operate the oxygen pump by applying a voltage just below the electrically decomposing voltage of the oxygen ion-conducting solid electrolyte body without using an external control device.

FIG. 7 shows a third embodiment of the oxygen sensor element according to the invention, which is a modified embodiment of FIG. 6. That is, oxygen sensor element 52 has the same structure as in the oxygen sensor element 51 except that a portion 67a between the points A and B conducted respectively with the conductive lead members 78, 79 of the pump electrodes 65, 66 is constructed by a part of the heating element 67. Moreover the portion 67a can be suitably set on any part of the heating element 67, for example, between points C and D, as shown in FIG. 7. However, it should be noted that it is necessary to ensure a direction of potential between the pump electrodes 65, 66 not to be reversed. In the latter case, since the potential of the point C is higher than that of the point D, the conductive lead member 78 of the pump electrode 65 is connected to the point C and the conductive lead member 79 of the pump electrode 66 is connected to the point D.

FIG. 8 shows a fourth embodiment of the oxygen sensor element according to the invention. In this embodiment, the oxygen sensor element 53 has a laminated structure of three oxygen ion-conducting solid electrolyte bodies 112 to 114, wherein the intermediate solid electrolyte body 113 is provided with an airtight space 115 extending in the longitudinal direction. This airtight space 115 is substantially maintained in the airtight state by bonding the solid electrolyte bodies 112 and 114 to both sides of the solid electrolyte body 113. In this case, it is preferable to make the intermediate solid electrolyte body 113 from a porcelain ceramic or to arrange a thin insulation layer between the solid electrolyte body 112 or 114 and the solid electrolyte body 113 except the position corresponding to the airtight space 115 to thereby electrically insulate the pump electrodes 119, 120 with respect to the measurement electrode 118 and the standard electrode 117. Thus, it is possible to eliminate dependency on a signal output of the oxygen sensor element due to a voltage applied to the pump electrodes 119 and 120. Moreover, it should be noted that the thin insulation layer may be arranged only to a portion where the temperature of the oxygen sensor element is above 250° C., because the oxygen ion-conducting solid electrolyte, such as zirconia stabilized with yttria, becomes substantially the insulator under 250° C.

As shown in FIG. 8, a resistance heating element 116 and a pump electrode 119 are arranged at a lower portion on a left surface of the solid electrolyte body 112. The pump electrode 119 is connected to the heating element 116 at a contact 116A. To both ends of the heating element 116 are connected lead members 124 and 125 which are arranged side by side to extend upward on the left surface of the solid electrolyte body 112. On the upper ends of the lead members 124 and 125 are formed connection terminals 124a and 125a of a connector (not shown) for connecting to an external circuit. Moreover, between the lead members 124 and 125 are arranged a lead wire 127, a lower end of which is further connected to the lead member 125. The heating element 116, the lead members 124, 125 except for the connection terminals 124a, 125a and the lead wire 127 are sandwiched between two thin ceramic films 121, which is arranged on and integrally united with the solid electrolyte body 112. In this case, one of the thin ceramic films 121 is provided at a position corresponding to the pump electrode 119 with a hole so as to directly contact the pump electrode 119 with the solid electrolyte body 112. Further, a protection layer 132 made of porous ceramics is arranged on the other thin ceramic film 121 having a hole for exposing the pump electrode 119 to the protection layer 132.

Another pump electrode 120 is arranged on the right side lower surface of the solid electrolyte plate 112 at a position opposite to the pump electrode 119. A lead member 126 connected to the pump electrode 120 extends on the lower surface of the solid electrolyte body 112 and is electrically connected with the lead wire 127 via a through-hole 122.

On the lower end portion of the left side surface of the solid electrolyte body 114 is arranged a standard electrode 117 facing the airtight space 115, while a measurement electrode 118 facing a substance to be measured is arranged on the lower end portion of the right side surface thereof at a position opposite to the standard electrode 117. Moreover, a lead member 128 connected to the standard electrode 117 extends upward on the left side surface of the solid electrolyte body 114, and is electrically conducted with a connection terminal 130 arranged on upper end portion of the right side surface of the solid electrolyte body 114 via a through-hole 123. Also, a lead member 129 connected to the measurement electrode 118 extends upward on the right side surface of the solid electrolyte body 114, and is connected to a connection terminal 131 arranged on the upper end portion of the right side surface of the solid electrolyte body 114.

In the oxygen sensor element 53 of FIG. 8, air is enclosed in the airtight space 115 in the manufacture of such an element, and thereafter oxygen is supplied to the airtight space 115 by applying a voltage to the pump electrodes 119 and 120. As shown in FIG. 8, the airtight space 115 has a volume extending substantially overall of the oxygen sensor element 53. Since this volume is relatively large, it is not necessary to always supply oxygen into the airtight space 115 by the operation of the oxygen pump. Further, since the airtight space 115 is maintained substantially in the airtight state (no substances other than oxygen is supplied therein), it is possible to prevent the occurrence of trobles in the oxygen sensor element 53 due to the intrusion of foreign matter such as water, sea water, etc. from the external atmosphere.

In the illustrated embodiment, since the pump electrodes 119 and 120 are connected to the heating element 116 or the lead member 125, it is not necessary to arrange another power source for the oxygen pump, and thus it is possible to make the connector of the oxygen sensor element small in size and to decrease the number of the connection terminals.

The volume of the airtight space 115 of FIG. 8 is necessary to be properly set by considering a gas temperature and a gas velocity at a position of the oxygen sensor element used (the element is easy to be cooled as the gas velocity increases). That is to say, the measurement electrode and the standard electrode are generally operative at a temperature above 350° C. to 400° C., so that the heater is sufficient to have a capacity for maintaining the oxygen sensor element above 400° C. under the lowest gas temperature. In other words, it is not preferable to keep the oxygen sensor element always above 500° C. (which is a temperature sufficiently operating the oxygen pump) by means of the heater because the excessive load is applied to the heater and the life of the heater is shortened.

As to a gasoline engine as an internal combustion engine of an automobile, in case of descending a steep slope, the temperature of the exhaust gas is lowered and thus the temperature of the oxygen sensor element is fairly decreased. The above mentioned state is not maintained for a long time and occurs for thirty minutes at most. Therefore, the airtight space must have a volume enough to hold oxygen corresponding to that consumed during this state.

For example, when the solid electrolyte body has an element length of 60 mm, a thickness of 0.4 mm and a width of 4 mm, since the airtight space is formed substantially over the whole length of the solid electrolyte plate, the volume of the airtight space is 2.5 mm in width $\times$ 60 mm in length $\times$ 0.4 mm in thickness $\cong$ 60 mm$^3$ (=60 $\mu$l). In this case, since a total impedance of a measurement device for a sensor output signal is generally about 1 M$\Omega$ and the sensor output is about 1 V, a current of 1 $\mu$A flows between the standard electrode 117 and the measurement electrode 118 and oxygen in the airtight space 115 is consumed correspondingly. In case that air is held in the airtight space 115, 50% of oxygen in air is consumed for about two hours but any effect on the sensor output is small. Therefore, a minimum volume of the airtight space may be assumed above 15 $\mu$l in view of its practical use.

As to the solid electrolyte having the oxygen ion conductivity, use may be made of zirconia containing yttria. The decomposing voltage of zirconia ($ZrO_2 \rightarrow Zr + O_2$) is slightly varied but is generally about 2.5 V. For example, if electrodes are arranged on both sides of the zirconia body and a voltage of 2.5 V is applied across these electrodes at about 500° C. without supplying oxygen from the external atmosphere, the zirconia is electrically decomposed to become black because oxygen is consumed by the electrolysis. In order to prevent the blackening of the zirconia body, it is necessary to control the voltage applied across the pump electrodes to be not more than 3 V (inclusive of voltage drop), preferably not more than 2.5 V. As a method for this control, it is designed to divide suitably the voltage applied to the heater (about 11 to 15 V in the automobile). In this case, there is an advantage that it is not necessary to use a controller or the like external to the oxygen sensor element. Further, a voltage is generated between the pump electrodes 119 and 120 due to a difference between internal and external oxygen partial pressure, and thus it is necessary to regard the thus generated voltage as the pump voltage. For example, since the output of the oxygen sensor is generally about 0.4 to 0.5 V on average per hour, it is possible to supply oxygen into the airtight space when the pump voltage is set about 0.5 V preferably above 1 V. Further, in case that it is necessary to use the through-hole for connecting the pump electrode to the heating element 116 as shown in FIG. 8, it is preferable to arrange the through-hole 122 to a position apart from the heating element 116. In this manner, it is possible to avoid the flowing of current through the solid electrolyte at the through-hole and the damage of through-hole due to a heat of the heater.

FIG. 9 shows a fifth embodiment of the oxygen sensor element according to the invention, which is a modified embodiment of FIG. 8. That is, the oxygen sensor element 54 has the same structure as in FIG. 8, except that an insulation layer 133 made of porcelain ceramic is arranged between the solid electrolyte bodies 112 and 113. The insulation layer 133 is provided with a slit 134 having a shape corresponding to that of the airtight space 115. Further, a porous portion 135 formed by incorporation of a porous ceramic is arranged in a part of the insulation layer 133. In this embodiment, the presence of the porous portion 135 makes its possible to discharge an excess amount of oxygen in the airtight space 115 to the external atmosphere. Therefore, it is possible to maintain an oxygen partial pressure in the airtight space 115 constant, and thus a measurement accuracy can be improved. Moreover, it is preferable to arrange the porous portion 135 at position exposed in the gas to be measured. Particularly it is possible to make the insulation layer 133 from the porous portion 135.

According to the invention, the airtight space is arranged in the casing for the oxygen sensor and communicated only with the gap of the oxygen sensor element facing the standard electrode, whereby, it is not required to arrange the hole for the supply of the standard substances as in the conventional oxygen sensor, and consequently the deterioration and damage of the oxygen sensor element due to the intrusion of foreign matter such as water, sea water and the like from the external atmosphere can completely be prevented.

Moreover, the oxygen pump is provided to supply oxygen into the airtight space, whereby oxygen as the standard substance can be sufficiently held in the airtight space. Further, since the volume of the airtight space can be made sufficiently large, it is not necessary to always operate the oxygen pump and thus the voltagge applied to the oxygen pump can be lowered. Moreover, since it is not necessary to always maintain the oxygen sensor element at high temperature by means of the heater, it is possible to make the heat input of the heater small and thus the deterioration of the oxygen sensor element can be mitigated.

Further, in the oxygen sensor element provided with the heater and at least one pair of the oxygen pump electrodes in addition to the standard electrode and the measurement electrode, at least one conductive lead member for the oxygen pump electrodes is connected to a part of the heater or the conductive lead member for the heater, whereby it is possible to use the same power source for the oxygen pump and for the heater and consequently the number of connection terminals for the external circuits which are formed at the end portion of the oxygen sensor element can be reduced correspondingly. In this case, since the number of the connection lines for the power source can be reduced, it is possible to reduce a probability of the broken wire and to make the connector small in size.

What is claimed is:

1. An oxygen sensor comprising:
    an oxygen sensor element comprising an oxygen ion-conducting solid electrolyte body having a standard electrode and a measurement electrode, each electrode being in contact with the solid electrolyte body, said solid electrolyte body further including a gap therein such that said standard electrode directly communicates with said gap;
    a casing which incorporates said element therein, said casing comprising an airtight space in communication with said gap, whereby said casing isolates at least said element from an external atmosphere; and at least one pair of oxygen pump electrodes for supplying oxygen to said airtight space by oxygen ion conduction through said solid electrolyte body.

2. An oxygen sensor according to claim 1, wherein said airtight space has a volume which is above 15 $\mu l$.

3. An oxygen sensor according to claim 1, wherein said oxygen sensor element further comprises a heater means for heating at least one of said standard electrode, measurement electrode and oxygen pump electrodes, and a means for dividing a voltage applied to said heater and for applying the divided voltage across said oxygen pump electrode.

4. An oxygen sensor according to claim 1, wherein said casing comprises:
- a protection tube including a protection cover portion for protecting a portion of said oxygen sensor element exposed to a gas to be measured and a protection cylinder portion for protecting a portion of said oxygen sensor element which does not face the gas to be measured;
- a housing for securing said oxygen sensor to a partition for isolating said gas to be measured from the external atmosphere;
- a seal member for inhibiting intrusion of the gas to be measured into said protection cylinder; and
- a stopper for plugging an end of said protection tube, said stopper having lead wires which run therethrough for electrically connecting said oxygen sensor element with an external circuit, whereby said airtight space is defined by said protection cylinder, seal member, stopper and oxygen sensor element.

5. The oxygen sensor according to claim 4, wherein said casing further comprises a partition arranged between said airtight space and said stopper for creating an airtight seal therebetween.

6. An oxygen sensor comprising:
- an oxygen sensor element comprising an oxygen ion-conducting solid electrolyte body having a standard electrode and a measurement electrode, each electrode being in contact with the solid electrolyte body, said solid electrolyte body further including a gap therein such that said standard electrode directly communicates with said gap;
- a casing which incorporates said element therein, said casing comprising an airtight space in communication with said gap, whereby said casing isolates at least said element from an external atmosphere;
- at least one pair of oxygen pump electrodes for supplying oxygen to said airtight space by oxygen ion conduction through said solid electrolyte body;
- a heater for heating at least one of said standard electrode, measurement electrode and oxygen pump electrodes; and
- a means for dividing a voltage applied to said heater and for applying the divided voltage to said pair of oxygen pump electrodes, said means being integrally formed with the oxygen sensor element.

7. An oxygen sensor element according to claim 6, wherein said heater has a positive resisitivity-temperature coefficient.

8. An oxygen sensor according to claim 6, wherein said oxygen sensor element has an elongated planar shape, said oxygen sensor element having a length of about 60 mm in its elongated direction.

9. The oxygen sensor according to claim 6, wherein said casing comprises:
- a protection tube including a protection cover portion for protecting a portion of said oxygen sensor element exposed to a gas to be measured and a protection cylinder portion for protecting a portion of said oxygen sensor element which does not face the gas to be measured;
- a housing for securing said oxygen sensor to a partition for isolating said gas to be measured from the external atmosphere;
- a seal member for inhibiting intrusion of the gas to be measured into said protection cylinder; and
- a stopper for plugging an end of said protection tube, said stopper having lead wires which run therethrough for electrically connecting said oxygen sensor element with an external circuit, whereby said airtight space is defined by said protection cylinder, seal member, stopper and oxygen sensor element.

10. The oxygen sensor according to claim 6, wherein said casing further comprises a partition arranged between said airtight space and said stopper for creating an airtight seal therebetween.

11. An oxygen sensor comprising:
- an oxygen sensor element comprising an oxygen ion-conducting solid electrolyte body having a standard electrode and a measurement electrode, each electrode being in contact with the solid electrolyte body, said solid electrolyte body further including a gap therein such that said standard electrode directly communicates with said gap;
- a casing which incorporates said element therein, said casing comprising an airtight space in communication with said gap, whereby said casing isolates at least said element from an external atmosphere and said airtight space has a volume which is above 15 $\mu l$;
- at least one pair of oxygen pump electrodes for supplying oxygen to said airtight space by oxygen ion conduction through said solid electrolyte body;
- a heater for heating at least one of said standard electrode, measurement electrode and oxygen pump electrodes; and
- a means for dividing a voltage applied to said heater and for applying the divided voltage to said pair of oxygen pump electrodes, said means being integrally formed with the oxygen sensor element.

12. The oxygen sensor according to claim 11, wherein said casing comprises:
- a protection tube including a protection cover portion for protecting a portion of said oxygen sensor element exposed to a gas to be measured and a protection cylinder portion for protecting a portion of said oxygen sensor element which does not face the gas to be measured;
- a housing for securing said oxygen sensor to a partition for isolating said gas to be measured from the external atmosphere;
- a seal member for inhibiting intrusion of the gas to be measured into said protection cylinder; and
- a stopper for plugging an end of said protection tube, said stopper having lead wires which run therethrough for electrically connecting said oxygen sensor element with an external circuit, whereby said airtight space is defined by said protection cylinder, seal member, stopper and oxygen sensor element.

13. The oxygen sensor according to claim 11, wherein said casing further comprises a partition arranged between said airtight space and said stopper for creating an airtight seal therebetween.

* * * * *